(12) United States Patent
SerVaas

(10) Patent No.: US 6,603,999 B2
(45) Date of Patent: Aug. 5, 2003

(54) VEHICULARLY INTEGRATED CARDIAC CARE SYSTEM

(75) Inventor: Paul SerVaas, Indianapolis, IN (US)

(73) Assignee: Benjamin Franklin Literary & Medical Society, Inc., Indianapolis, IN (US)

( * ) Notice: Subject to any disclaimer, the term of this patent is extended or adjusted under 35 U.S.C. 154(b) by 149 days.

(21) Appl. No.: 09/850,827

(22) Filed: May 8, 2001

(65) Prior Publication Data

US 2002/0169482 A1 Nov. 14, 2002

(51) Int. Cl.[7] .................................................. A61N 1/39
(52) U.S. Cl. ............................................................ 607/5
(58) Field of Search ............................................. 607/5

(56) References Cited

U.S. PATENT DOCUMENTS

| | | | |
|---|---|---|---|
| 4,566,457 A | 1/1986 | Stemple | 128/419 |
| D285,915 S | 9/1986 | Luthe et al. | D12/192 |
| 4,834,103 A | 5/1989 | Heath | 128/798 |
| 5,405,361 A | 4/1995 | Persson | 607/5 |
| 5,573,300 A * | 11/1996 | Simmons | 296/197 |
| 5,775,456 A | 7/1998 | Reppas | 180/322 |
| 5,792,190 A | 8/1998 | Olson et al. | 607/5 |
| 5,946,605 A * | 8/1999 | Takahisa et al. | 455/66 |
| 5,959,577 A | 9/1999 | Fan et al. | 342/357.13 |
| 6,026,292 A | 2/2000 | Coppinger et al. | 455/406 |
| 6,070,932 A * | 6/2000 | Lopez-Baquero et al. | 296/146.9 |
| 6,073,007 A | 6/2000 | Doyle | 455/412 |
| 6,090,056 A * | 7/2000 | Bystrom et al. | 601/1 |
| 6,101,413 A | 8/2000 | Olson et al. | 607/5 |
| 6,119,039 A | 9/2000 | Leyde | 607/5 |
| 6,142,962 A | 11/2000 | Mollenauer et al. | 607/41 |
| 6,199,099 B1 | 3/2001 | Gershman et al. | 709/203 |
| 6,208,256 B1 | 3/2001 | Fleming et al. | 340/632 |
| 6,208,897 B1 | 3/2001 | Jorgenson et al. | 607/5 |
| 6,254,159 B1 * | 7/2001 | Wieczorek et al. | 296/19 |
| 6,480,744 B2 * | 11/2002 | Ferek-Petric | 607/60 |

* cited by examiner

Primary Examiner—Carl Layno
(74) Attorney, Agent, or Firm—William F. Bahret (57) ABSTRACT

A cardiac care system integrated with a vehicle is provided wherein regularly included vehicle components are used in the system, where available. The cardiac care system includes an automated external defibrillator integrated with the vehicle so as to be readily available when needed. The vehicle battery is shared with the defibrillator to charge the defibrillation capacitor. A connector in the passenger compartment of the vehicle makes high voltage from the capacitor available inside the vehicle. Instructions are broadcast by the computer controlling the defibrillator over the regularly included vehicle speakers. A wireless communication system connecting the cardiac care system to outside help may be included.

32 Claims, 8 Drawing Sheets

VEHICULARLY INTEGRATED CARDIAC CARE SYSTEM

FIELD OF THE INVENTION

The present inventions pertain to emergency medical equipment. More particularly, the present inventions relate to a vehicularly integrated automated cardiac response equipment for emergency situations.

DESCRIPTION OF THE PRIOR ART

Sudden cardiac arrest (SCA) occurs to one American nearly every minute of every day. Of those experiencing sudden cardiac arrest, more than 95 percent die. SCA occurs when the heart muscle fibers contract chaotically rather than in synch with each other, making it unable to pump blood. SCA survival rates increase dramatically when there is early access to a defibrillator. Statistically, every minute the patient goes without defibrillation the chance of survival decreases by ten percent.

Sudden cardiac death has become such a major health problem in America that federal legislation was passed to address the issues SCA raised. The Cardiac Arrest Survival Act requires the Secretary of Health and Human Services to develop recommendations and guidelines for placement and use of automated external defibrillators (AEDs) in federal buildings. The Act additionally augments existing state "Good Samaritan" laws by ensuring the federal liability protection for users and purchasers of AEDs.

Prior to the use of AEDs, only trained medical professionals were able to interpret the heart rhythms on manual defibrillator devices. AEDs use computer technology to analyze the rhythms instantly and accurately, making it possible for non-medical professionals with relatively minimal training to perform defibrillation on a SCA victim. AEDs implemented in Chicago's O'Hare International Airport have helped save eleven lives from 1999 to the present. Additionally, AEDs have been placed in other public places, such as malls, and have been carried by emergency fire and police response teams.

An AED is a relatively simple device including a battery, a capacitor, a computer processor, software, a speaker and two high voltage electrodes. Many AED's do not have visual displays and have only one button to turn the device on or off. Disposable electrode pads used by the AED can be purchased separately at most drug stores. Portable AEDs are currently manufactured by AGILENT TECHNOLOGIES, MEDTRONIC PHYSIO-CONTROL CORP., MEDICAL RESEARCH LABORATORIES, INC., and SURVIV-ALINK CORP.

Of the estimated 1000 SCA attacks that occur each day in America, perhaps dozens occur while the victim is driving. A portion of these attacks result in the injury or deaths of other motorists or bypassers. When carried by people potentially at risk, mobile AEDs are often relegated to the vehicle's trunk. Thus, when needed, valuable time is lost retrieving and setting up the AED. There is a need for an AED that is readily available inside the passenger compartment of the vehicle.

Recently, computer functionality has been integrated with vehicle stereo modules to provide increased vehicle passenger compartment functionality and communications. In November of 1999, FREIGHTLINER CORPORATION introduced the TRUCK PRODUCTIVITY COMPUTER™, a vehicle on-board computer module using the WINDOWS CE™ operating system. The module included AM/FM stereo, weather band receiver, compact disc player/drive, wireless communication system, and GPS. The wireless communication system is used to transmit messages and data via satellite or cellular networks.

What is needed is an integrated on-board vehicle computer system that can detect and process the cardiac state of the patient, and provide life saving cardiac assistance. What is additionally needed is a vehicle based AED which would encourage motorists in early stages of a heart attack to pull over, call 911 and put on the electrodes. Further, a low cost way to incorporate an AED and other cardiac lifesaving equipment into a motor vehicle is needed which makes AEDs more available when needed.

These objects, and others, are satisfied by Applicant's present inventions disclosed herebelow.

SUMMARY OF THE INVENTION

One embodiment of the present inventions relates to a cardiac care system integrated with a vehicle. The cardiac care system makes use of a vehicle battery located in the engine compartment or, in some cars, the trunk of the vehicle. The cardiac care system additionally includes at least one high voltage defibrillator capacitor, a defibrillator charging circuit connected between said vehicle battery and said at least one defibrillator capacitor and a defibrillator electrode connector located external to the vehicle's engine compartment. A computer for receiving electrical signals input to said defibrillator electrode connector, and for controlling the discharge of a defibrillator capacitor is additionally included. Another embodiment includes a communication system for connecting the cardiac care system with a remote location.

Related objects and advantages of the present invention will be apparent from the following description.

BRIEF DESCRIPTION OF THE DRAWINGS

The present inventions are illustrated by way of example, and not by way of limitation, in the figures of the accompanying drawings and in which like reference numerals refer to similar elements and in which.

DESCRIPTION OF THE PREFERRED EMBODIMENTS

For the purposes of promoting an understanding of the principles of the inventions, reference will now be made to the embodiments illustrated in the drawings and specific language will be used to describe the same. It will nevertheless be understood that no limitation of the scope of the inventions is thereby intended, such alterations and further modifications of the principles of the inventions as illustrated therein being contemplated as would normally occur to one skilled in the art to which the inventions relate.

In accordance with one embodiment of the present inventions, there is provided an intelligent cardiac care system including an automated external defibrillator integrated with a vehicle in such a way as to make the devices less expensive and more commonly available. The cardiac care system of the present inventions comprises existing vehicle components, when available, to reduce the cost of the device.

Figure 1:
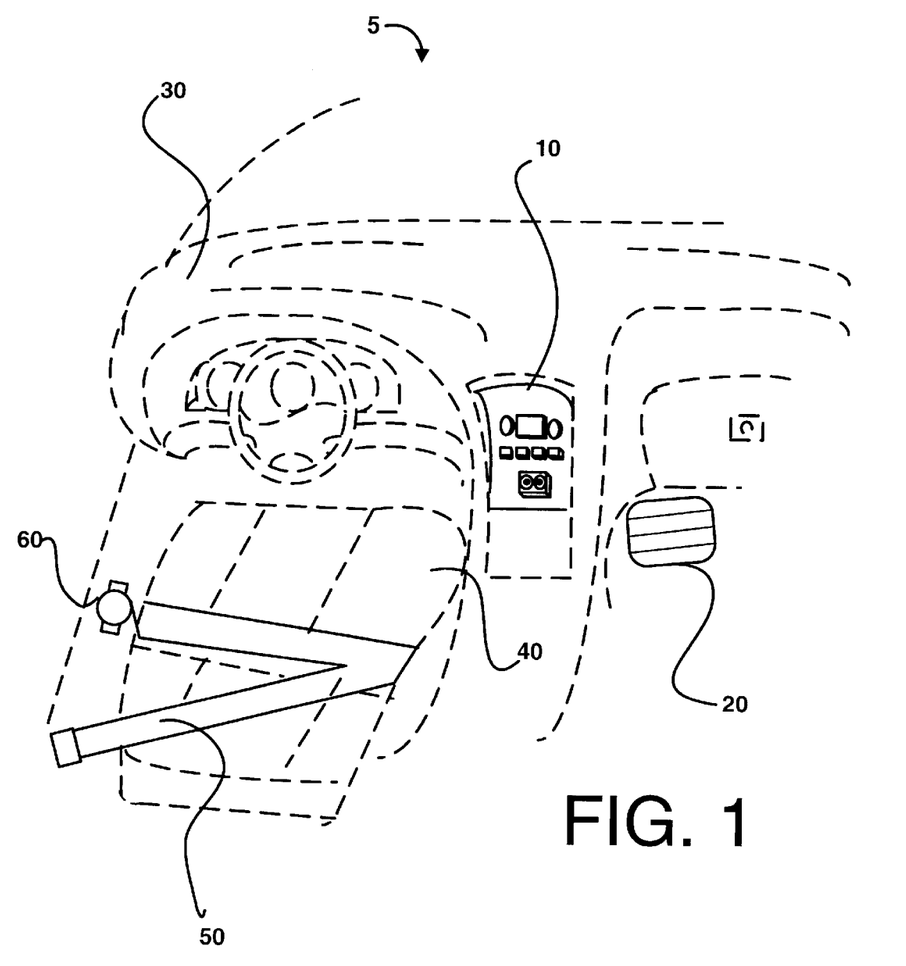
FIG. 1 shows a perspective partial view of the passenger compartment of a vehicle in accordance with one embodiment of the present invention.

Referring now to FIG. 1, there is shown a partial perspective view of the passenger compartment of a vehicle 5 incorporating one embodiment of the present inventions. Vehicle 5 includes a dashboard mounted automated external defibrillator (AED) interface module 10. In the present embodiment, AED interface module 10 acts as the vehicle's standard radio/stereo/entertainment unit but additionally includes a microprocessor and software for use in defibrillation, as well as a connector for defibrillation electrodes to interface with the module 10. The AED interface module 10 provides an audio output on the standard vehicle speakers 20. The AED interface module 10 may be mounted into the vehicle dashboard 30, as shown, or may be mounted in some other location. Additionally, the vehicle 5 includes a passenger seat 40 and a safety restraint belt 50. Although the safety restraint belt 50 is shown as a three point belt, other restraint systems may be used with the cardiac care system of the present invention. Additionally, seat motor 60 for adjusting the front driver's side seat is included.

Figure 2:
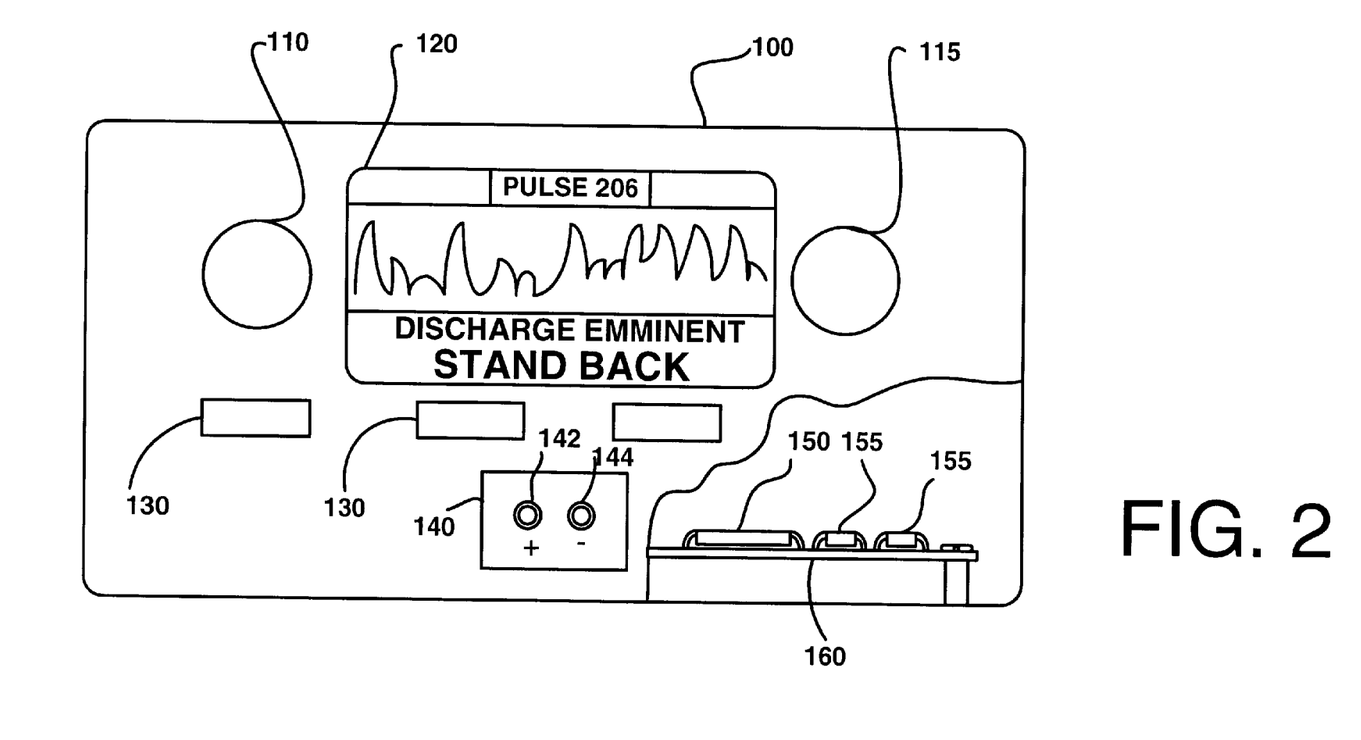
FIG. 2 shows a perspective partial view of one embodiment of a vehicle component incorporating cardiac life saving functionality.

Referring now to FIG. 2, there is shown a partial perspective view of an AED interface module 10 integrated with a vehicle stereo, which may be used in the system of FIG. 1. AED interface module 10 includes standard am/fm stereo components, such as an on/off/volume knob 110, a tuning knob 115, a display 120 and pretuned setting buttons 130. However, the AED interface module additionally includes AED electrode connector 140, which includes a positive (anode) electrode female connector 142 and a negative (cathode) electrode female connector 144. The AED electrode connector 140 includes insulated high voltage wires that simply pass through the interface module 100, exit its rear and subsequently pass through the firewall separating the passenger and engine compartments and connect to a high voltage AED capacitor.

The AED interface module 10 includes a microprocessor 150 and microprocessor memory 155 internally mounted to PCB 160. Microprocessor memory 155 includes software for controlling the microprocessor to process information received via the electrode connectors 142 and 144 and to make a determination whether defibrillation is appropriate. If affirmative, the software controlled microprocessor will cause the capacitor to deliver the defibrillation pulse. Additionally, the microprocessor controls the delivery of instructions for using the defibrillator, which may be delivered audibly over the stereo speakers (20 of FIG. 1) and/or, optionally, on the stereo display, 120. Such software can be the same or similar to that currently included in AEDs on the market, such as the software that operates the LIFEPAK® 500 AED by MEDTRONIC PHYSIO-CONTROL. As shown in FIG. 2, the AED software and display 120 can additionally be adapted to display information derived from signals received by the AED electrodes.

As an alternate to integrating the AED interface module with the vehicle stereo, an integrated all-in-one module, such as the TRUCK PRODUCTIVITY COMPUTER™ used in FREIGHTLINER CORPORATION vehicles may be modified to include the electrode connectors 142 and 144, and the AED software to interpret signals received from the electrodes and to make and implement a defibrillation decision.

The TRUCK PRODUCTIVITY COMPUTER™ announced by FREIGHTLINER includes a HITACHI SH4 166 MHz processor, two Universal Serial Bus connections, an RS-232 serial port that connects the unit to satellite systems, cellular modems and other existing wireless equipment, a vehicle information display measuring 80 pixels in height and 320 pixels in width (⅙ VGA by ½ VGA), AM/FM Stereo Receiver and Compact Disc Player/Drive, and GPS locator. Additionally, the system can be linked to the vehicles data link (SAE J1587) to provide information on vehicle status, fuel usage, engine operation and diagnostics.

Figure 3:
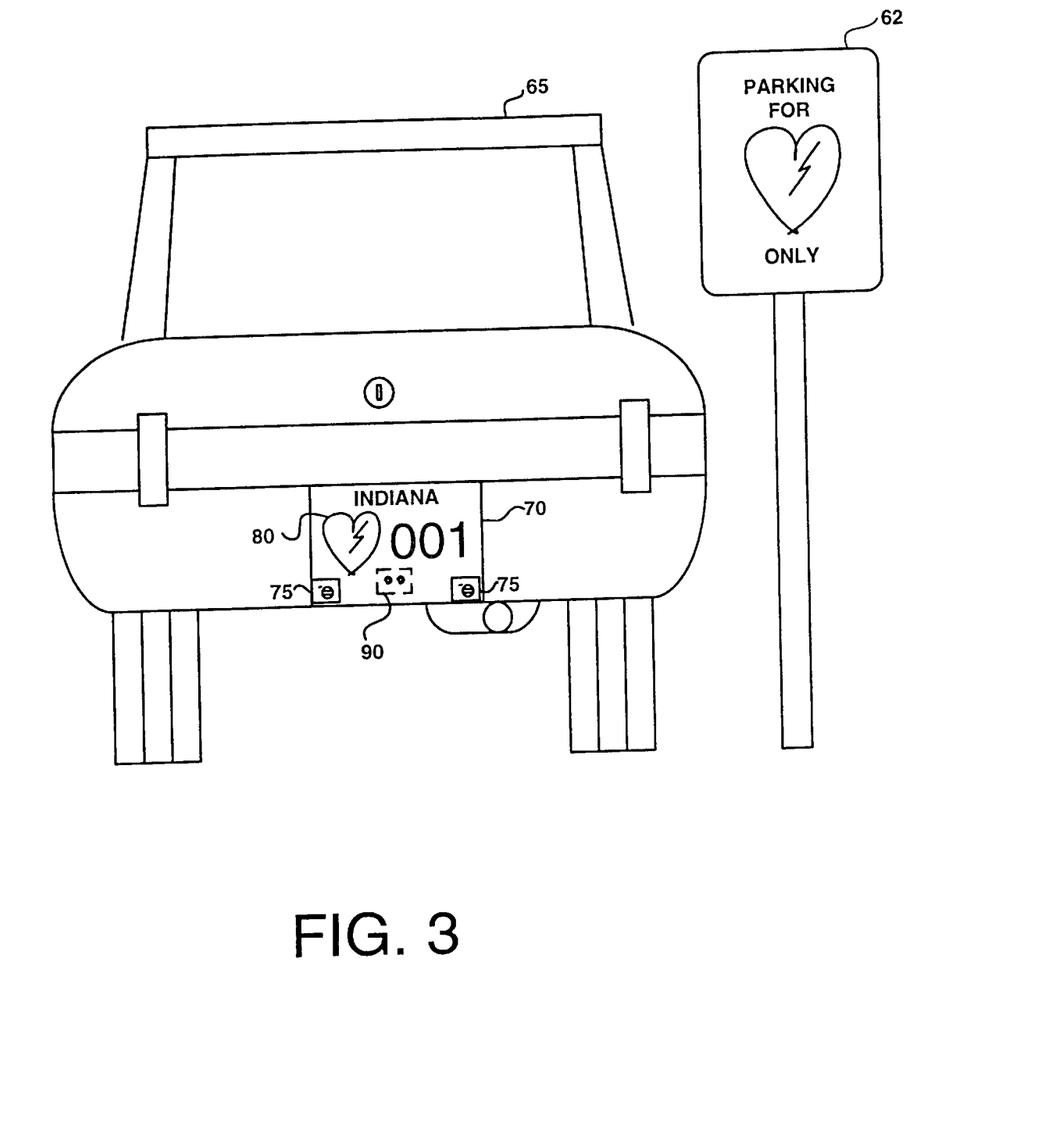
FIG. 3 shows a perspective view of a vehicle in accordance with one embodiment of the present invention.

Additionally, it would be useful to provide an electrode jack external to the vehicle for access by others in an emergency situation. Referring now to FIG. 3, there is shown a vehicle 65 incorporating one embodiment of the present inventions. Although a car is shown, this is not meant to be limiting. It can be seen from the present descriptions that the present inventions can be integrated into any vehicle, including a car, passenger bus and/or truck.

The vehicle 65 includes an external AED electrode connector 90 located behind the license plate 70. The license plate 70 is secured to the vehicle using the hinged brackets 75. As depicted in FIG. 3, the license plate 70 may include a particular universally adopted symbol, such as the heart/bolt symbol 80, identifying the vehicle as one including a defibrillator. Alternatively, a vehicle including an external AED electrode connector may sport a bumper sticker or other indicator signaling the availability of the defibrillator.

Figure 5:
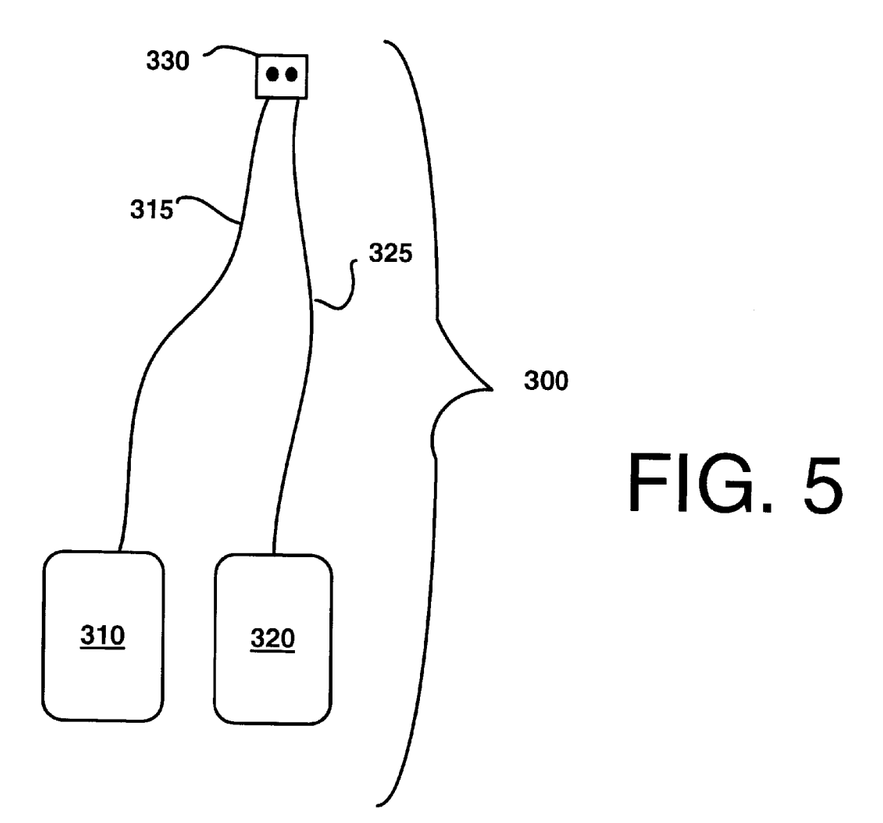
FIG. 5 shows a block diagram depicting electrodes useful with the present inventions.

The external AED electrode connector 90 may be identical to that of AED electrode connector 140 of FIG. 2, including anode and cathode electrode connectors. In use, the license plate 70 is tilted down on hinges 75 to expose the external AED electrode connector 90. An electrode packet, such as is shown in FIG. 5, may be stored behind the license plate for use in connection with external AED electrode connector 90 if desired. Additional electrodes may be stored in the glove box or otherwise inside the passenger compartment of the vehicle. An external electrode connector may be located at other locations accessible outside the vehicle.

Figure 4:
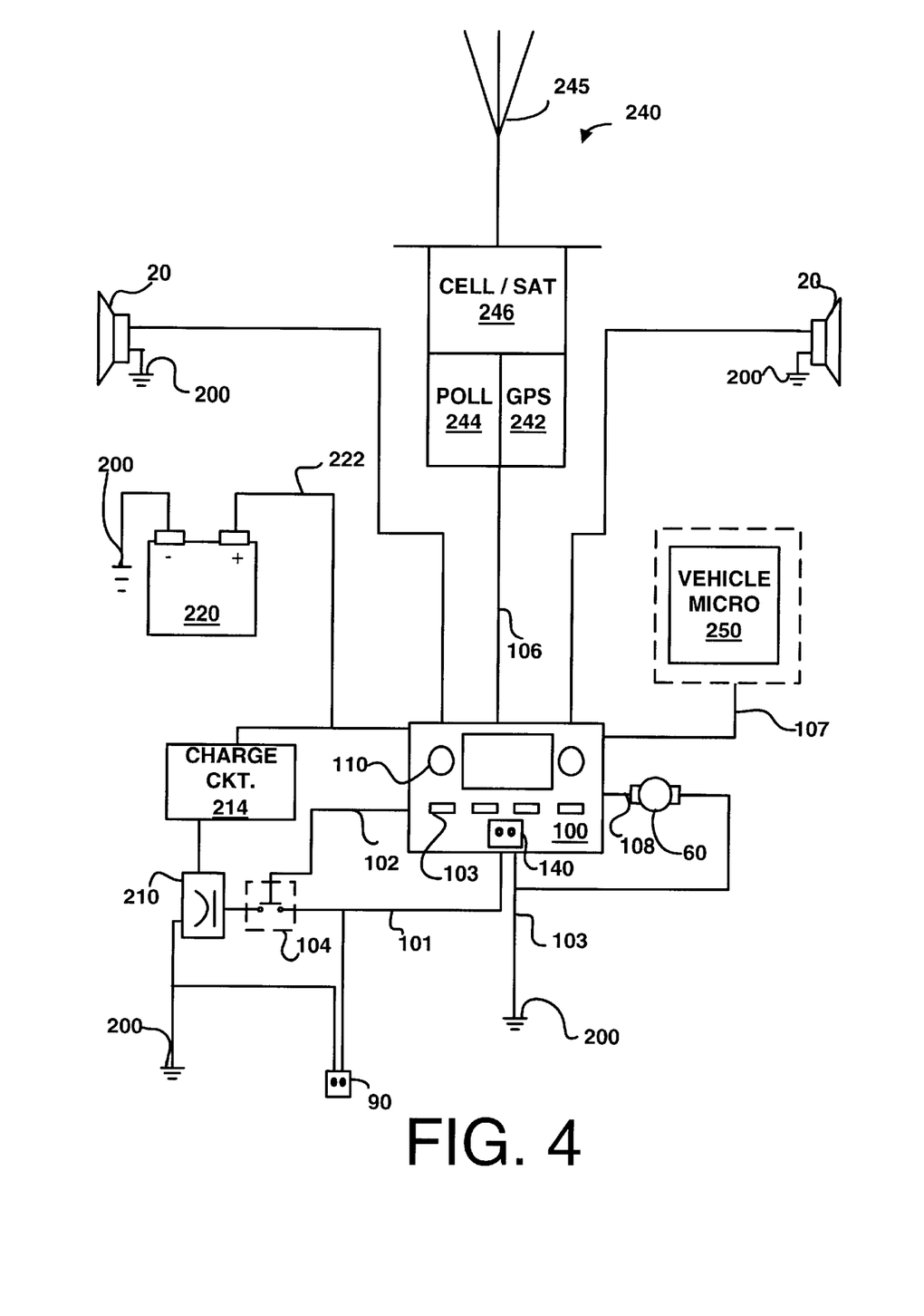
FIG. 4 shows an electrical block diagram depicting the major electrical interconnections of the integrated vehicular system in accordance with one embodiment of the present inventions.

Referring now to FIGS. 4 and 5 there is shown an electrical block diagram depicting the major electrical interconnections of an integrated vehicular cardiac care system in accordance with one embodiment of the present inventions and a block diagram depicting electrodes useful with the present inventions. The AED interface module 100 includes, as described above in connection with FIG. 2, the microprocessor and software for operating the vehicle integrated AED and the electrode interface connector 140. Alternatively, all cars built since Jan. 1, 1996 have OBD-II on-board diagnostic system computers. As such, if desired, the software for the AED processing and control can be incorporated into the existing vehicle OBD-II microcomputer 250, which is optionally in communication with the AED interface module 100 via data bus 107.

At least high voltage wire 101 extends through the firewall of the vehicle passenger compartment and into the engine compartment, thus making high voltage available in the vehicle passenger compartment. Wire 103 is connected to the vehicle ground 200. High voltage wire 101 is connected from the cathode of the AED connector 140 to the vehicle ground 200. The anode terminal of the AED interface connector 140 is connected to the AED capacitor 210, via insulated high voltage wire 101. AED capacitor 210 may be any type of defibrillator energy discharge capacitor, or a bank of such capacitors, such as those made by CSI CAPACITORS of 810 Rancheros Drive, San Marcos, Calif. Electrodes 300 include a connector 330 that mates with the interface connectors 90 and 140. Electrodes 310 and 320 are connected to the connector 330 by insulated high voltage wires 315 and 325, respectively. Electrodes 300 can be a disposable electrode set, such as that shown in U.S. Pat. Nos. 4,834,103 or 5,402,884, those patents incorporated by reference herein or those provided for use with the Physio-Control LIFEPAK AED.

The AED capacitor 210 is additionally connected to the positive terminal of the external AED interface connector 90. The AED interface module 100 is powered by the vehicle battery 220 regardless of the position of the key ignition switch or the state of the on/off/volume knob 110. AED interface module 100 would additionally include a "sleep mode" so as to not drain the battery when not in use. In one embodiment of the present inventions, plugging in the electrodes (300 of FIG. 5) to either the connectors 90 or 140 would close a bypass switch causing power to be applied the AED interface module 100 even when the on/off switch 110 is in the "off" position.

The AED capacitor 210 can store and deliver a charge of between 4800–7500 volts to the positive high voltage electrode of the connector 140 and/or 90. AED capacitor 210 is charged by the vehicle battery 220 via line 222. By using the vehicle battery, the dashboard mounted unit would not need its own battery. The vehicle battery may be located in the ordinary vehicle battery location, such as the engine compartment, or in some vehicles, in the trunk.

Further, the dash mounted unit would not need to include a recharging circuit for charging the battery. Instead the host vehicle's battery would be kept charged by the host vehicle's existing alternator. Further, unlike portable hand carried AEDs on the market, the dashboard mounted unit would not include a means to proactively detect a dead battery. Instead the dashboard mounted unit would depend on the fact that the host vehicle's battery is massively oversized for repeatedly recharging an AED capacitor. The unit would also benefit from the manual battery testing that is effectively performed every time a motorist starts a car containing a vehicle integrated AED in accordance with the present embodiment. Using the host vehicle's battery, the AED capacitor would recharge faster than existing hand carried AED's.

The capacitor 210 may be discharged by closing switch 104. Switch 104 may be closed by manually pushing a button on the front of the AED electrode interface module 100, such as button 103. If desired, the computer may automatically control when switch 104 is closed, via control line 102. Additionally, as will be explained below, the computer may additionally control the closing of switch 104 (and thus the discharge of capacitor 210) in response to a remote signal to discharge the capacitor. By manually closing the switch using button 103, there is the opportunity to ensure that all bystanders/good Samaritans that may be assisting in CPR are clear at the time the capacitor is discharged. The automatic mode is useful in cases where the victim is alone in the vehicle, and possibly unconscious. Additionally, when used in the manual mode, the computer may still be used to determine when the button 103 is to be pushed. Additionally, the computer would announce via the speakers 20 when the button is to be pushed in the manual mode. For example, in the manual mode the computer may announce in a synthesized or prestored voice or using the display, "stand clear and push button now." In the computer controlled modes, the computer may instruct a bystander or good samaritan to "stand clear" in a synthesized or prestored voice, or using the display.

Interposed between battery 220 and capacitor 210 is a charging circuit 214 to step up the voltage from 12 volts to the required AED pulse voltage and keep the capacitor charged. As such, high voltage in the thousands of volts is available in the passenger compartment of the car from the AED capacitor 210, via the AED interface connector 140. The AED interface module 100 controls the discharge of the capacitor 210, via line low voltage control line 102. Other forms of charging circuits and arrays of capacitors may be used. For example the charging circuit and capacitor array shown in U.S. Pat. No. 5,405,361 to Persson may be used, if desired. U.S. Pat. No. 5,405,361 is incorporated herein by reference.

The AED of the present invention is further integrated with the vehicle in that the AED audio commands and instructions are broadcast from the AED interface module 100 through the vehicle's existing stereo speakers 20. As such, the dashboard mounted AED interface module need not include speakers of its own. The volume level over the speakers may be set using volume knob 110. As noted above, alternatively the AED interface module may take over when in use and override the volume/on/off settings of knob 110 to ensure that the instructions can be heard over speakers 20, even when the radio was off. In such a system, the AED interface connectors 140 and/or 90 would include a bypass switch such that upon plugging electrodes into the connectors 140 or 90, a circuit bypassing the on/off switch of the AED interface module 100 would be closed, connecting the AED interface module 100 directly to the vehicle battery 220. Additionally, if the external electrode connector 90 were used, once the vehicle license plate was tilted down, the instructions would play on the unoccupied vehicle's stereo at full volume, regardless of the setting of knob 110, so as to be heard outside the car. Additionally, if tied to the movement of the license plate on hinges 75, playing the instructions at full volume may additionally deter the theft of electrodes from behind the license plate of the vehicle.

If desired, the integrated vehicular cardiac care system of the present inventions could include automatic motorized CPR belts capable of compressing a heart attack patient's chest in a beneficial way. Such automated systems are shown, for example in U.S. Pat. Nos. 6,142,962 and 6,066,106, those patents incorporated by reference herein. Referring now to FIGS. 1 and 4, there is shown the motor 60, which may be used to cause the seatbelt 50 of the vehicle 5 to selectively compress the chest of the patient, while seated in the vehicle seat 40. The motor 60 would be powered by the vehicle battery 220. Further the motor 60 may be a separate motor added to the seatbelt assembly for the present purpose or may be the existing motor used in some cars for adjusting the front passenger and the driver's car seat. If the existing car seat motor is used, then a housing for the motor would be adapted so that the seat belt could be fed onto a roller in the housing to cause the motor to drive the seatbelt compressions. Additionally, the motor would receive driving signals from the AED system microprocessor (150 of FIG. 2 or 250 of FIG. 4).

Further, the cardiac care system of the present inventions may optionally include a communication unit 240 in communication with the microprocessor of the AED interface module 100 via data bus 106. If the TRUCK PRODUCTIVITY COMPUTER is used, a separate wireless communication system may be omitted, as wireless communication is already provided in that unit.

Figure 6:
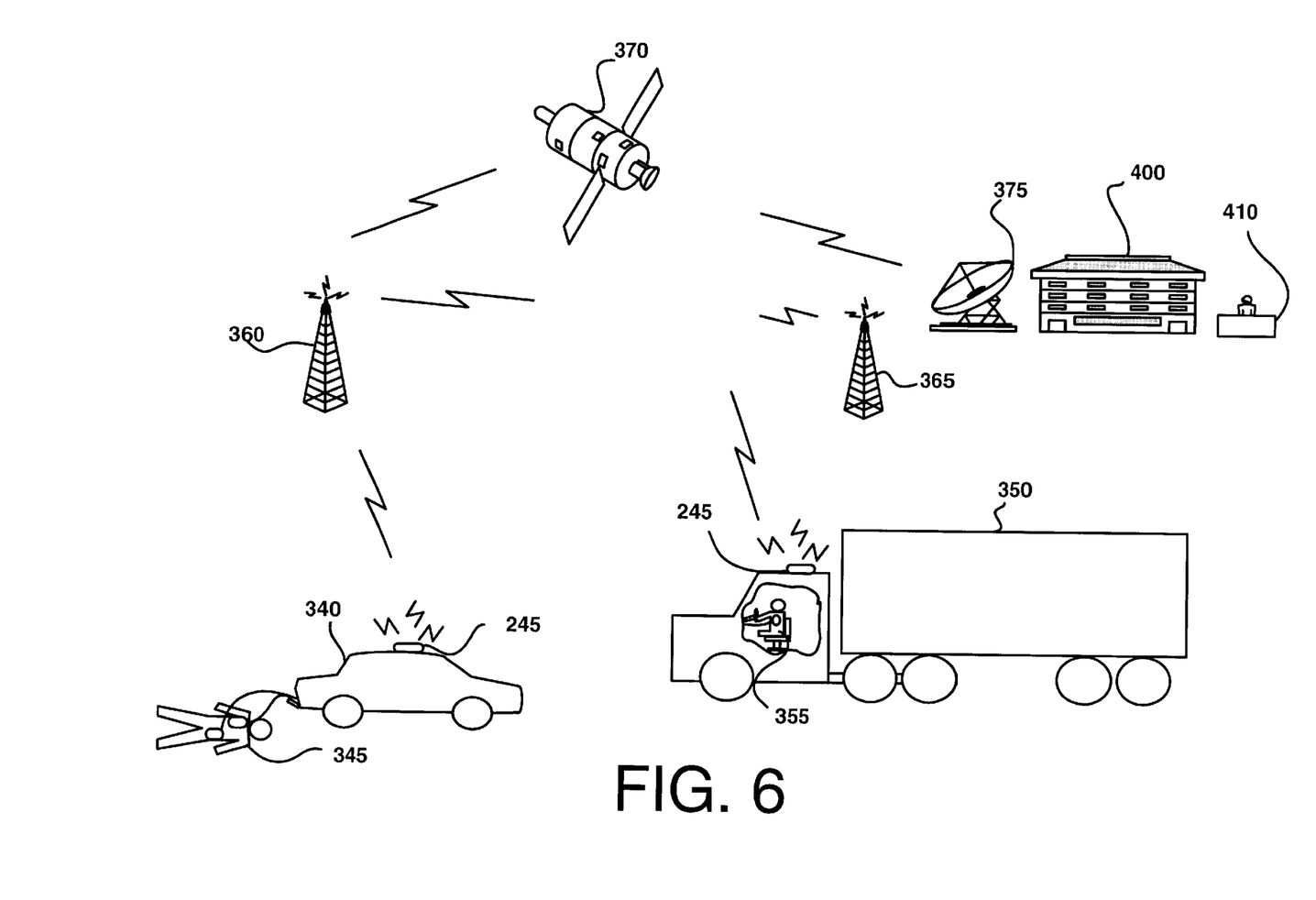
FIG. 6 is a block diagram of a vehicularly integrated cardiac care system in accordance with one embodiment of the present inventions.

Referring now to FIGS. 4 and 6, communication unit 240 receives instructions from the microcomputer (150 of FIG. 2) housed in the AED interface module 100 or, in one embodiment, from the vehicle micro 250. The system may be set up to automatically dial 911 on a cellular/satellite unit 246 when electrodes 300 are plugged into the AED interface connector 140. A pre-stored message may be transmitted to an emergency dispatcher relating the emergency condition. Additionally location information derived from GPS unit 242 may be transmitted as part of the message. Alternatively, communications unit 240 may include a satellite communication device, such as made by QUALCOMM INCORPORATED. Such devices and systems that may be incorporated with the present inventions are shown in U.S. Pat. Nos. 6,026,292 and 6,073,007, which are incorporated herein by reference.

Figure 7:
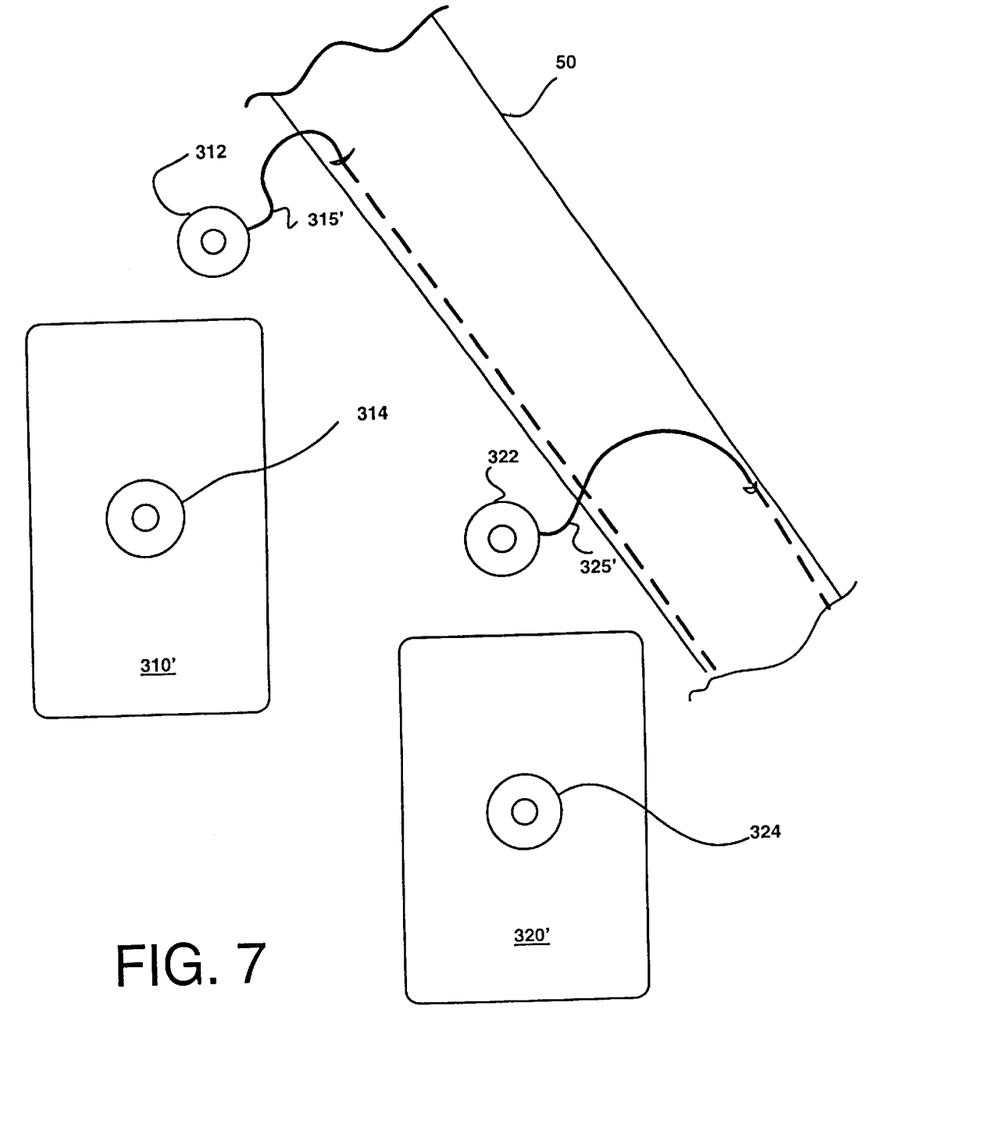
FIG. 7 shows a perspective partial view of a seatbelt incorporating electrode wires and connectors in accordance with one particular embodiment of the present inventions.

In use, the communication system 240 can relay information about the condition of a patient to a central station (400 of FIG. 6) such as a hospital or trucking fleet management center via antenna 245. More specifically, referring to FIG. 6, there is shown a vehicle 340 having a patient 345 bearing electrodes (such as 300 of FIG. 5) which are connected to the external connector (90 of FIG. 4) of the vehicle 340. The communication system 240 of the vehicle 340 may transmit via cell phone connection information relating to the patient 345. The information is transmitted from the antenna 245 to the cell tower 360 and via the cell network to a hospital or central station 400, via cell tower 365. Similarly, vehicle 350 includes a driver 355 who is wearing the electrode assembly (300 of FIG. 5). Information about the physiological condition of the driver 355 is being relayed by antenna 245 to the satellite 370 and from the satellite 370 to the hospital or central station 400, via the satellite dish 375. Satellite 370 may be a cellular or mobile communication satellite or may be a proprietary satellite, such as used by QUALCOMM or HUGHES. Once information is relayed to the central station 400, an emergency professional 410 at the central station 400 can evaluate the situation and dispatch emergency equipment to the patient/driver, or otherwise provide the patient/driver with services or information. Note that in such a system where the vital signs of a driver, such as a long-haul driver, are monitored remotely, the electrodes may be worn at all times and not just during cardiac emergencies. This continuously provides the central station with vital statistics about the vehicle operator, as is currently done with astronauts. Further, in a system where the vital statistics of the vehicle operator are continuously monitored, it is possible to incorporate thin line electrode wires into the seatbelt of the vehicle. As such, referring now to FIG. 7 there is shown a partial perspective view of a seat belt 50 incorporating therein defibrillator electrode wires 315' and 325', which are substantially similar to electrode wires 315 and 325 of FIG. 5. The wires 315' and 325' may have the major length of the wire sewn into or otherwise concealed in the seatbelt material yet have the connector ends exiting the seatbelt in appropriate locations that would match up with the locations of electrodes 310' and 320' worn by the user when the seatbelt is properly engaged. Electrode connectors or snaps 312 and 322 would detachably mate with the appropriate pad connectors or snaps 314 and 324, thus permitting the user to easily disconnect the wires to exit the vehicle. Pads 310' and 320' are similar to pads 310 and 320 of FIG. 5, and may be worn under the shirt of the user, wherein wires 315' and 325' may be connected to the pads 310' and 320' through or under the user's shirt. The ends of the wires remote from the connectors 312 and 322 may engage a connector, such as connector 330 of FIG. 5, and may be used in a system as described in connection with FIGS. 4 and 6. Thus, the vital statistics of the vehicle operator may be continuously monitored without seriously affecting the operator's ability to exit the vehicle. Wires 315' and 325' and pads 310' and 320' including quick disconnect terminals may be similar to those used in the Heartstart 911 AED product manufactured by In one embodiment of the present inventions, the vehicularly integrated AED device could include a manual mode wherein the microprocessor does not make the decision to discharge the capacitor. Rather, in such a manual mode the system uses the cell/sat modem 246 to call a doctor or other emergency professional 410 located at the hospital or central station 400 and the doctor, after reviewing vital signs relayed by the system, could trigger the discharge of the AED capacitor, when appropriate. Such triggering can be accomplished using a remote phone keypad code, or the physicians telemedicine receiver terminal.

Further, the communication unit (240 of FIG. 4) of the vehicle integrated cardiac care system may optionally include a radio frequency polling receiver 244. Radio frequency polling receiver 244 would receive an approved distress signal which is broadcast in a parking location to locate a vehicle including an AED device. The polling receiver 244 would communicate the signal to the microprocessor in the AED interface module 100 and/or the vehicle microprocessor 250. The polling signal would be processed and a preset message announcing the presence of the vehicle integrated defibrillator would be broadcast over the vehicle speakers 20 at top volume. Alternatively, the system could be tied into an existing car alarm, to cause the car alarm to go off in response to the polling signal. The person searching for an AED integrated vehicle would then have access to the AED through the external AED interface connector 90 behind the license plate. Additionally, the vehicle stereo would announce instructions over the speakers 20, while the rear AED interface connector 90 is in use, notwithstanding the vehicle ignition is turned off.

Figure 8:
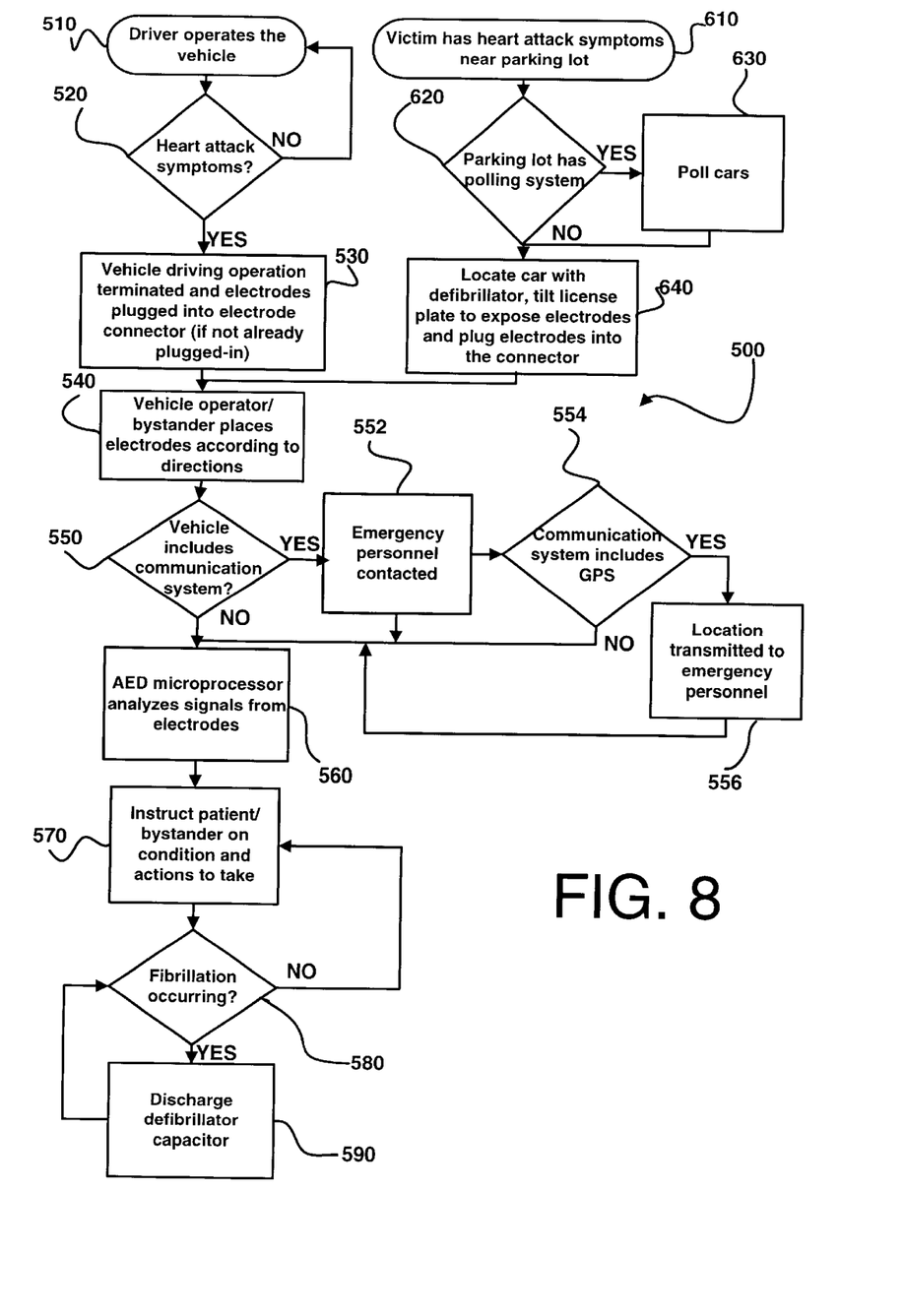
FIG. 8 is a flow diagram of the operation of the integrated vehicular system in accordance with the present inventions.

Referring now to FIG. 8 there is shown a flow diagram 500 of one particular use of the present inventions. A driver operates the vehicle which the vehicle battery used to charge the AED capacitor (step 510). While driving it may be determined whether physical symptoms the driver or a passenger were experiencing could be symptoms of an oncoming heart attack (step 520). If so, the driver would drive the vehicle to the shoulder of the road or to an available parking lot and plug in the AED electrodes, if the electrodes are not already plugged in (step 530). As noted herein, the electrodes may be stored in the glove compartment of the vehicle and may be plugged into a connector in the AED interface module (100 of FIG. 2). This would enable the AED to be readily available to a person in the passenger compartment of the vehicle. The victim or an assistant would then place the electrodes on the patient according to placement directions (step 540). Note that many of the electrode packages on the market have graphical indications of where to place the electrodes printed directly on the electrodes. Alternatively, once the electrodes are plugged into the connector, the AED interface module processor may display or announce via the vehicle speakers, directions for placing the electrodes.

If the vehicularly integrated cardiac care system includes the optional communication system (240 of FIG. 4) then emergency personnel would be contacted to give instructions or otherwise communicate with the victim (step 552), for example via cell phone or email messages. If the system includes an optional GPS module, than the location of the victim could be transmitted to the emergency personnel (step 556).

After placement of the electrodes, the AED microprocessor analyzes signals from the electrodes (step 560). Instructions for the patient or information relating to the detected condition are displayed on the interface module display and/or verbally announced via the vehicle's speakers (step 570). If the patient is in fibrillation, the AED microprocessor analyzes the heart rhythms and determines the best time to discharge the capacitor. Additionally, the microprocessor controls the discharge of the capacitor. After discharge, the capacitor is automatically recharged by the vehicle battery, until the vehicle battery is drained.

Similarly, if the vehicle is already parked and a victim has heart attack symptoms in or near the parking lot (step 610), the victim can have access to a defibrillator in the parking lot. If the parking lot and the car include the optional polling equipment (244 of FIG. 4) the parking lot or garage attendant can use a radio transmitter to poll the cars (step 630). The victim and/or the attendant can locate the car with the defibrillator, either by sound if the car and lot have a polling system, or by checking the cars for a specialized license plate, bumper sticker or other indicator of a car possessing the defibrillator. Additionally, in the future, parking lots may include a parking space in a desirable location reserved for vehicles incorporating an integrated AED device accessible from outside the vehicle. These parking spaces, if marked and standardized like handicapped parking spaces, would cut down on the time it takes to locate an AED integrated vehicle by giving victims and bystanders a standard place to first check. Additionally, offering a desirable parking spot marked for AED vehicles only (such as 62 of FIG. 3) would reward owners of AED integrated vehicles and be sufficient incentive for them to park in those spaces reserved for AEDs. This incentive is similar to the government's existing tax credit to persons owning watercraft which are volunteered for government use during war times.

After the car is located, if the external AED connector is behind the license plate, the license plate is tilted down exposing the electrodes and connector and the electrodes are plugged into the connector (step 640), after which time steps 540–590 may be performed.

From the above, it can be seen that the present inventions provide a more cost effective life saving device which shares existing components of the vehicle to provide cardiac care in emergency situations. While the inventions have been illustrated and described in detail in the drawings and foregoing description, the same is to be considered as illustrative and not restrictive in character. For example, it can be seen that the optional wireless communication and/or seatbelt compression components can be omitted and the disclosed inventions would still provide life saving assistance in an emergency situation. It should be understood that only the preferred embodiments have been shown and described and that all changes and modifications that come within the spirit of the invention are desired to be protected.

What is claimed is:

1. A cardiac care system integrated with a vehicle, comprising:
   a vehicle battery for the vehicle;
   at least one high voltage defibrillator capacitor;
   a defibrillator charging circuit connected between said vehicle battery and said at least one defibrillator capacitor;
   a defibrillator electrode connector located external to the vehicle's engine compartment, at least one terminal of which receives the discharge from said at least one high voltage defibrillator capacitor; and
   a computer for receiving electrical signals input to said defibrillator electrode connector.

2. The cardiac care system of claim 1, additionally including at least a pair of defibrillator electrodes which detachably engage said defibrillator electrode connector.

3. The cardiac care system of claim 2, wherein said computer additionally processes said electrical signals to determine when said at least one capacitor should be discharged.

4. The cardiac care system of claim 3, wherein said computer initiates the discharge of said at least one defibrillator capacitor based said on electrical signals from said defibrillator electrode connector.

5. The cardiac care system of claim 3, additionally including a switch for semi-automatically initiating the discharge of said at least one capacitor, wherein said computer provides instructions on when to close the switch.

6. The cardiac care system of claim 5, wherein said computer additionally controls the broadcast of instructions over the vehicle's existing speakers.

7. The cardiac care system of claim 6, wherein said defibrillator electrode connector is integrated with the vehicle's stereo unit in the passenger compartment of the vehicle.

8. The cardiac care system of claim 7, wherein said computer is integrated with the vehicle's entertainment unit.

9. The cardiac care system of claim 8, wherein said stereo unit additionally includes a visual display for displaying instructions relating to defibrillation.

10. The cardiac care system of claim 1, wherein said computer is the vehicle's onboard diagnostics computer.

11. The cardiac care system of claim 2, wherein said defibrillator electrode connector is located external to said vehicle.

12. The cardiac care system of claim 7, wherein the vehicle additionally includes an external defibrillator electrode connector external to said vehicle.

13. The cardiac care system of claim 12, wherein said cardiac care system includes an indicator for indicating the presence of the cardiac care system.

14. The cardiac care system of claim 13, wherein the indicator is a visual indicator external to the vehicle.

15. The cardiac care system of claim 13, wherein the indicator is an audible indicator which activates in response to a radio frequency polling request initiated external to the vehicle.

16. The cardiac care system of claim 3, including a motor connectable to at least one seat belt in the vehicle, said motor controlled by said computer to provide CPR compressions to the chest of a patient using said at least one seat belt.

17. The cardiac care system of claim 1, further including a communication unit to connect said computer to a remote location.

18. The cardiac care system of claim 17, wherein the vital signs of a patient received by said computer via said electrodes are monitored at said remote location.

19. The cardiac care system of claim 18, wherein the discharge of said at least one defibrillator capacitor is controlled from said remote location.

20. The cardiac care system of claim 17 wherein said communication system additionally includes GPS to provide said remote location with a location signal of the vehicle.

21. A cardiac care system integrated with a vehicle, comprising:

a vehicle battery for the vehicle;

at least one high voltage defibrillator capacitor;

a defibrillator charging circuit connected between said vehicle battery and said at least one defibrillator capacitor;

a defibrillator electrode connector located external to the vehicle's engine compartment, at least one terminal of which receives the discharge from said at least one high voltage defibrillator capacitor;

a computer for receiving electrical signals input to said defibrillator electrode connector;

at least a pair of defibrillator electrodes which detachably engage said defibrillator electrode connector;

at least one seatbelt; and at least one electrode wire incorporated in said seatbelt and connected to said defibrillator electrode connector.

22. A method of providing cardiac care to a person, comprising:

providing a vehicle including a vehicle battery located in the engine compartment of the vehicle, at least one high voltage defibrillator capacitor, a defibrillator charging circuit connected between said vehicle battery and said at least one defibrillator capacitor, a defibrillator electrode connector located external to the vehicle's engine compartment, an insulated high voltage wire connected from said at least one defibrillator capacitor to said defibrillator electrode connector, and a computer for receiving electrical signals input to said defibrillator electrode connector, said computer additionally for controlling the discharge of said at least one defibrillator capacitor;

providing defibrillator electrodes comprising at least two electrode pads and an electrode plug, said electrode plug removably engaged with said defibrillator electrode connector;

placing electrodes on the person;

analyzing signals from said electrodes; and discharging said at least one capacitor in response to said analyzing step.

23. The method of claim 22, additionally comprising the step of communicating said signals from said electrodes to a remote location.

24. The method of claim 23 wherein said discharging step is controlled from said remote location.

25. The method of claim 22, wherein said discharging step is controlled by said computer.

26. The method of claim 22, wherein said electrode connector is located in the passenger compartment of said vehicle.

27. The method of claim 26, wherein said electrode connector is located in the dashboard of said vehicle.

28. The method of claim 27, wherein said computer additionally controls the broadcast of instructions over the vehicle's existing speakers.

29. The method of claim 28, wherein said vehicle additionally includes an external defibrillator connector, external to said vehicle.

30. The method of claim 29, wherein said vehicle includes an indicator indicating the presence of said at least one defibrillator capacitor.

31. The method of claim 30, wherein said indicator is a visual indicator.

32. The method of claim 30, wherein said indicator is an audio indicator, and wherein said method further includes remotely polling said computer to activate said audio indicator.

* * * * *